United States Patent [19]

Grasselli et al.

[11] 4,156,660

[45] May 29, 1979

[54] CATALYST USEFUL FOR THE MANUFACTURE OF ACRYLONITRILE AND METHACRYLONITRILE

[75] Inventors: Robert K. Grasselli, Garfield Heights; Arthur F. Miller, Cleveland; Harley F. Hardman, Lyndhurst, all of Ohio

[73] Assignee: The Standard Oil Company, Cleveland, Ohio

[21] Appl. No.: 885,136

[22] Filed: Mar. 10, 1978

Related U.S. Application Data

[62] Division of Ser. No. 410,516, Oct. 29, 1973, abandoned, which is a division of Ser. No. 112,780, Feb. 4, 1971, abandoned.

[51] Int. Cl.$^2$ ............................................. B01J 27/16
[52] U.S. Cl. .................................... 252/437; 252/435; 252/468
[58] Field of Search .................... 260/465.3; 252/435, 252/437, 468

[56] References Cited

U.S. PATENT DOCUMENTS

| | | | |
|---|---|---|---|
| 3,086,041 | 4/1963 | Hadley et al. | 260/465.3 |
| 3,226,422 | 12/1965 | Sennewald et al. | 252/437 X |
| 3,288,721 | 11/1966 | Kerr | 252/435 |
| 3,346,617 | 10/1967 | Hiroki et al. | 252/468 |
| 3,347,902 | 10/1967 | Grasselli et al. | 252/437 X |
| 3,415,886 | 12/1968 | McClellan | 252/437 X |
| 3,576,764 | 4/1971 | Yamaguchi et al. | 252/437 |
| 3,642,930 | 2/1972 | Grasselli et al. | 252/437 X |
| 3,778,386 | 12/1973 | Takenaka et al. | 252/437 X |

*Primary Examiner*—Patrick Garvin
*Attorney, Agent, or Firm*—David J. Untener; Herbert D. Knudsen; Larry W. Evans

[57] ABSTRACT

High yields of unsaturated nitriles are obtained by the oxidation of olefin-ammonia mixtures in the presence of a catalyst comprising the oxides of bismuth, molybdenum, iron and at least one element of the Group II B metals as essential components, and optionally the oxides of cobalt, nickel, phosphorus, arsenic and an alkali metal.

6 Claims, No Drawings

CATALYST USEFUL FOR THE MANUFACTURE OF ACRYLONITRILE AND METHACRYLONITRILE

This is a divisional of application Ser. No. 410,516 filed Oct. 29, 1973, now abandoned which was a divisional of application Ser. No. 112,780 filed Feb. 4, 1971, now abandoned.

This invention relates to an improved process and catalyst for the oxidation of olefin-ammonia mixtures to unsaturated nitriles, and more particularly to an improved process and catalyst for the oxidation of propylene-ammonia and isobutylene-ammonia to acrylonitrile and methacrylonitrile, respectively. The oxidation is conducted in the presence of a catalyst consisting essentially of the oxides of bismuth, molybdenum and iron in combination with at least one element of the Group II metals as essential ingredients, and optionally the oxides of the elements of cobalt, nickel, phosphorus, arsenic and an alkali metal.

The catalyst employed in the process of this invention has a high activity for the production of unsaturated nitriles at a lower reaction temperature than is normally employed for this type of process. In addition to high activity for nitrile production, the catalyst has a number of other important advantages that contribute greatly to the efficient and economic operation of the process. The catalyst has excellent redox stability under the reaction conditions of the process. This permits the use of low process air to olefin ratios and high weight hourly space velocities. The catalyst exhibits efficient ammonia utilization thus greatly reducing the amount of unreacted ammonia appearing in the reactor effluent and thus lowering the amount of sulfuric acid required to neutralize the ammonia in the effluent. This results in improvements in the operation of the recovery section of the process and in improved pollution control resulting from the lowering of polymer waste products that are formed. The catalyst performs optimally at a lower reactor temperature than is normally employed for this type of reaction, and the use of lower operating temperatures favors longer catalyst life and minimizes effluent problems such as afterburning. Despite the lower reaction temperatures per pass conversions to the nitrile product as high as 80 percent and above are obtained. A further important advantage associated with the catalyst of this invention is the low cost of the essential catalytic components and the ease of catalyst preparation.

The high activity of this catalyst at a low reaction temperature and at a low bismuth content is surprising in view of the disclosure in U.S. Pat. No. 2,904,580 issued Sept. 15, 1959, which describes a process for the production of acrylonitrile from propylene and ammonia in the presence of a catalyst selected from the group consisting of bismuth, tin and antimony salts of molybdic and phosphomolybdic acids and bismuth phosphotungstate, and U.S. Pat. No. 3,226,422 issued Dec. 28, 1965, which discloses a catalyst containing the oxides of iron, bismuth, molybdenum, and phosphorous for the production of unsaturated nitriles from olefin-ammonia mixtures.

The reactants employed in producing the unsaturated nitriles of this invention are oxygen, ammonia, and an olefin having three carbon atoms in a straight chain such as propylene or isobutylene, and mixtures thereof. The olefins may be in admixture with paraffinic hydrocarbons, such as ethane, propane, butane and pentane; for example, a propylene-propane mixture may constitute the feed. This makes it possible to use ordinary refinery streams without special separation. Likewise, diluents such as nitrogen and the oxides of carbon may be present in the reaction mixture without deleterious effect.

In its preferred aspect, the process comprises contacting a mixture comprising propylene or isobutylene, ammonia and oxygen with the catalyst at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 0.5:1 to 4:1 and a ratio of about 1:1 to 3:1 is preferred.

The molar ratio of ammonia to olefin in the feed to the reaction may vary between about 0.5:1 to 5:1. There is no real upper limit for the ammonia-olefin ratio, but there is generally no reason to exceed a ratio of 5:1. At ammonia-olefin ratios appreciably less than the stochiometric ratio of 1:1, various amounts of exygenated derivates of the olefin will be formed. Outside the upper limit of this range only insignificant amounts of aldehydes and acids will be produced, and only very small amounts of nitriles will be produced at ammonia-olefin ratios below the lower limit of this range. It is surprising that within the ammonia-olefin range stated, maximun utilization of ammonia is obtained, and this is highly desirable. It is generally possible to recycle any unreacted olefin and unconverted ammonia.

We have found that in some cases water in the mixture fed to the reaction vessel improves the selectivity of the reaction and yield of nitrile. However, addition of water to the feed is not essential in this invention, inasmuch as water is formed in the course of the reaction.

In general, the molar ratio of added water to olefin, when water is added, is above about 0.25:1. Ratios on the order of 1:1 to 4:1 are particularly desirable, but higher ratios may be employed, i.e., up to about 10:1.

The reaction is carried out at a temperature within the range of from about 500° to about 1100° F. The preferred temperature range is from about 600° to 900° F.

The pressure at which reaction is conducted is another variable, and the reaction is carried out at about atmospheric or above atmospheric (2 to 5 atmospheres) pressure.

The apparent contact time is not critical, and contact times in the range of from 0.1 to about 50 seconds may be employed. The optimum contact time will, of course, vary depending upon the olefin being reacted, but in general, a contact time of from 1 to 15 seconds is preferred.

Generally any apparatus of the type suitable for carrying out oxidation reactions in the vapor phase may be employed in the execution of this process. The process may be conducted either continuously or intermittently. The catalyst bed may be a fixed-bed employing a large particulate or pelleted catalyst or, alternately a so-called "fluidized" bed of catalyst may be employed. The fluid reactor may comprise an open column or the reactor may contain a plurality of perforated trays stacked horizontally throughout the length of the column, as described in U.S. Pat. No. 3,230,246 issued Jan. 18, 1966.

The reactor may be brought to the reaction temperature before or after the introduction of the reaction feed mixture. However, in a large scale operation it is preferred to carry out the process in a continuous manner, and in such a system the circulation of the unreacted olefin is contemplated. Periodic regeneration or reactivation of the catalyst is also contemplated, and this may be accomplished, for example, by contacting the catalyst with air at an elevated temperature.

The products of the reaction may be recovered by any of the methods known to those skilled in the art. One such method involves scrubbing the effluent gases from the reactor with cold water or an appropriate solvent to remove the products of the reaction. If desired, acidified water can be used to absorb the products of reaction and neutralize unconverted ammonia. The ultimate recovery of the products may be accomplished by conventional means. The efficiency of the scrubbing operation may be improved when water is employed as the scrubbing agent by adding a suitable wetting agent in the water. Where molecular oxygen is employed as the oxidizing agent in this process, the resulting product mixture remaining after the removal of the nitriles may be treated to remove carbon dioxide with the remainder of the mixture containing the unreacted olefin and oxygen being recycled through the reactor. In the case where air is employed as the oxidizing agent in lieu of molecular oxygen, the residual product after separation of the nitriles and other carbonyl products may be scrubbed with a non-polar solvent, e.g., a hydrocarbon fraction in order to recover unreacted olefin and in this case the remaining gases may be discarded. The addition of a suitable inhibitor to prevent polymerization of the unsaturated products during the recovery steps is also contemplated.

The catalyst useful in the process of the present invention is a mixture, compound or possibly complex of the oxides of iron, bismuth, molybdenum, and at least one element selected from Group II of the Periodic Classification, and optionally the oxides of nickel or cobalt or both, phosphorus and/or arsenic, and an alkali metal. The composition is conveniently expressed in the following empirical formula:

$A_a B_b C_c D_d Fe_e Bi_f Mo_g O_x$ wherein A is an alkali metal, B is one or more of the elements selected from the group consisting of nickel and cobalt, C is phosphorus or arsenic or both, and D is at least one element selected from Group II A and Group II B of the Periodic Classification of elements, and wherein (a) is a number from 0 to less than 0.1, (b) is a number from 0 to 12, (c) is a number from 0 to 3, (d) is a number from 0.1 to 10, (e) and (f) are each a number from 0.1 to 6, (g) is a number from 8 to 16, and (x) is a number determined by the valence requirements of the other elements present. A preferred catalyst composition is one in which A is potassium, D is magnesium, and the atom ratios of the elements in the foregoing empirical formula are within the range wherein (a) is a number of 0 to 0.09, (b) is from 1 to 6, (c) is from 0 to 1, (d) is a number from 0.1 to 7, (e) and (f) are each a number of from 1 to 4, and (g) is 12.

The catalyst of this invention may be prepared by any of the numerous methods of catalyst preparation which are known to those skilled in the art. For example, the catalyst may be manufactured by co-precipitating the various ingredients. The co-precipitated mass may then be dried and ground to an appropriate size. Alternately, the co-precipitated material may be slurried and spray-dried in accordance with conventional techniques. The catalyst may be extruded as pellets or formed into spheres in oil as is well-known in the art. Alternatively, the catalyst components may be mixed with the support in the form of the slurry followed by drying, or they may be impregnated on silica or other supports.

A particularly attrition-resistant form of the catalyst may be prepared by adding the support material to the catalyst in two stages, first by preparing and heat-treating a mixture of active catalyst components and from 0 to 60% by weight of the total support material, followed by adding the remainder of the support material to the powdered form of the heat-treated catalyst. A more detailed description of the preparation of an attrition-resistant catalyst may be obtained from the examples.

The alkali metal may be introduced into the catalyst as an oxide or as any salt which upon calcination will yield the oxide. Preferred salts are the nitrates which are readily available and easily soluble.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the iron component into the catalyst one may use any compound of iron which, upon calcination, will result in the oxides. As with the other elements, water-soluble salts are preferred for the ease with which they may be uniformly dispersed within the catalyst. Most preferred is ferric nitrate. Cobalt, nickel and the Group II metals may be similarly introduced. However, the Group II metals may also be introduced into the catalyst as the insoluble carbonates or hydroxides which upon heat-treating result in the oxides.

To introduce the molybdenum component, any molybdenum oxide such as the dioxide, trioxide, pentoxide, or sesquioxide may be used; more preferred is a hydrolyzable or decomposable molybdenum salt such as a molybdenum halide. A preferred starting material is ammonium heptamolybdate.

Arsenic may be introduced as orthoarsenic acid. Phosphorus may be introduced as an alkali metal, an alkaline earth metal or the ammonium salt, but is preferably introduced as phosphoric acid.

Other elements may be introduced, starting with the metal, oxidizing the metal with an oxidizing acid such as nitric acid, and then incorporating the nitrate into the catalyst. Generally, however, the nitrates are readily available and form a very convenient starting material.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result in the oxides of the instant catalyst upon heating to a temperature within the range disclosed hereinafter.

The catalyst can be employed without a support and will display excellent activity. The catalyst can also be combined with a support, and preferably it is combined with at least 10 percent up to about 90 percent of the supporting compound by weight of the entire composition. Any known support materials can be used, such as, for example, silica, alumina, zirconia, titania, alundum, silicon carbide, alumina-silica, the inorganic phosphates such as aluminum phosphate, silicates, aluminates, borates, carbonates, and materials such as pumice, montmorillonite, and the like that are stable under the reaction conditions to be encountered in the use of the catalyst.

The catalytic activity of the system is enhanced by heating at an elevated temperature. Generally, the catalyst mixture is dried and heated at a temperature of from about 500° to about 1850° F., preferably at about 900° to 1300° F., for from about one to twenty-four hours or more. If activity then is not sufficient, the catalyst can be further heated at a temperature above about 1000° F. but below a temperature deleterious to the catalyst.

In general, activation of the catalyst is achieved in less time at higher temperatures. The sufficiency of activation at any given set of conditions is ascertained by a spot test of a sample of the material for catalytic activity. Activation is best carried out in an open chamber, permitting circulation of air or oxygen, so that any oxygen consumed can be replaced.

Further, pre-treatment or activation of the catalyst before use with a reducing agent such as ammonia in the presence of a limited amount of air at a temperature in the range of 500° to 1000° F. is also beneficial.

A preferred method of preparing the catalyst of this invention and a more complete description of the process of the invention can be obtained from the following examples. In addition to the production of unsaturated nitriles, the catalyst of this invention is also useful for the conversion of olefins, such as propylene and isobutylene, to the corresponding unsaturated aldehydes and unsaturated carboxylic acids.

EXAMPLES 1 TO 18, AND 20 TO 22

The catalysts employed in the examples of this invention were prepared by essentially the same procedure as described herein below, using the appropriate starting materials.

A catalyst having the composition 80 wt.%—$Mg_{4.5}Fe_4Bi_2P_{0.5}Mo_{12}O_{51}$—20 wt.%—$SiO_2$ was prepared by dissolving 70.6 grams of $(NH_4)_6Mo_7O_{24}.4H_2O$ in water with a minimum amount of heating. To this were added in succession with stirring 1.9 grams of $H_3PO_4$ (85 wt.%) and 76.7 grams of DuPont Ludox AS (30 wt.%) colloidal silica sol. The solution was stirred for 15 minutes at room temperature. 53.7 Grams of $Fe(NO_3)_3.9H_2O$ dissolved in water were added to this solution followed by the successive addition of 38.5 grams of $Mg(NO_3)_2.6H_2O$, and 32.4 grams of $Bi(NO_3)_3.5H_2O$ dissolved in water containing 8 cc of concentrated $HNO_3$ (68 wt.%). The slurry was heated with constant stirring until gel formation occurred. The gel was then dried at approximately 270° F. The resulting catalyst was heat-treated at 600° F. for 5 hours and then at 1020° F. for 20 hours, and was then sized to 20–35 Tyler screen mesh.

EXAMPLE 19

An attrition-resistant catalyst having the composition 60 wt.%—$Mg_{4.5}Ni_{2.5}Fe_3BiP_{0.5}Mo_{12}O_{51}$—40 wt.%—$SiO_2$ was prepared by dissolving 706 grams of $(NH_4)_6Mo_7O_{24}.4H_2O$ in 570 cc of water, using minimum heating, and then blending with 19 grams of 85% $H_3PO_4$. To this solution were added 743 grams of 30 percent silica sol (Du Pont AS Ludox), followed by the successive addition of 242 grams of $Ni(NO_3)_2.6H_2O$ dissolved in water, and while maintaining vigorous agitation, an aqueous solution containing 404 grams of $Fe(NO_3)_3.9H_2O$ in 190 cc water, and an aqueous solution containing 385 grams of $Mg(NO_3)_2.6H_2O$ in 190 cc water. To this was added a solution composed of 162 grams of $Bi(NO_3)_3.5H_2O$, 20 cc of 68% $HNO_3$ and 190 cc of water. The slurry was heated with stirring until a non-fluid cake was obtained. The solid was then treated at a temperature of 600° F. for a period of 5 hours. After pulverizing the dry solid mechanically, 1000 grams of powder were blended with 1115 grams of 30% silica sol (Du Pont AS Ludox) and sufficient water to result in a 45 wt.% solids slurry. The blend was ball-milled in a porcelain ball-mill for 20 hours. The resulting slurry was then spray-dried in a 4½ foot diameter Bowen spray-drier with an inlet temperature of 550° F. and an outlet temperature of 350° F. The microspheroidal product from the spray-drier was put into a furnace at 280° F. The temperature was raised to 600° F. over a period of one hour and maintained at that temperature for three hours. A final calcination of 17 hours duration at 1150° F. was imposed upon the catalyst prior to charging the material to the reactor for testing.

The reactor employed in carrying out the ammoxidation reactions in Examples 1 through 22 was a standard reactor with a fixed catalyst bed. The catalyst volume was about 5 cc and the catalyst mesh size was 20 to 35 Tyler screen mesh. The gases were metered to the reactor with rotameters. The products of the reaction were recovered by scrubbing the effluent gases from the reactor with water and hydrochloric acid and were then analyzed by means of a gas chromatograph.

In the examples given, percent conversion to the unsaturated nitrile is defined as follows:

Mole percent per pass conversion to unsaturated nitrile = (Mols of nitrile product obtained/Mols of olefin fed) × 100

Ammoxidation reactions carried out with the catalyst compositions of this invention employing propylene and isobutylene as the hydrocarbon feeds are summarized in Tables I and II, respectively. These data are compared with conversions obtained with catalyst compositions of the prior art disclosed in U.S. Pat. No. 2,904,580 and U.S. Pat. No. 3,226,422, and shown in Examples 1 and 2 of Table I and in Example 20 of Table II. The date in these tables show that per pass conversions to acrylonitrile and methacrylonitrile obtained with catalysts of the present invention are substantially higher than those obtained with catalysts of the prior art. Comparable results to those shown in Tables I & II were also obtained with these catalysts in a fluid bed reactor.

TABLE I

CONVERSION OF PROPYLENE TO ACRYLONITRILE
Fixed-Bed Reactor
Reaction Temperature: 750° F.  Pre-Run Time: 15 minutes
Contact Time: 2.9 seconds  Run Time: 30 minutes
Feed Ratio (Molar): $C_3^=/NH_3/Air = 1/1.5/5/11$

| Example | Catalyst Composition | (Mole Basis) % Per Pass Conversion to Acrylonitrile |
|---|---|---|
| 1  | 50%-$Bi_9PMo_{12}O_{52}$-50% $SiO_2$ | 39.9 |
| 2  | 50%-$Fe_{4.5}Bi_{4.5}PMo_{12}O_{52}$-50% $SiO_2$ | 41.9 |
| 3  | 80%-$Mg_{6.5}Fe_3Bi_1P_{0.5}Mo_{12}O_{50}$-20% $SiO_2$ (b) | 59.1 |
| 4  | 80%-$Mg_{4.5}Fe_4Bi_2P_{0.5}Mo_{12}O_{51}$-20% $SiO_2$ (a) | 65.3 |
| 5  | 100%-$Mg_{4.5}Fe_4Bi_2P_{0.5}Mo_{12}O_{51}$ (b) | 67.9 |
| 6  | 80%-$K_{0.07}Mg_{4.5}Fe_4Bi_2P_{0.5}Mo_{12}O_{51}$-20% $SiO_2$ | 63.9 |
| 7  | 80%-$Mg_{4.5}Fe_4Bi_2As_{0.5}Mo_{12}O_{51}$-20% $SiO_2$ (b) | 65.9 |
| 8  | 80%-$Mg_{4.5}Fe_4Bi_2Mo_{12}O_{49}$-20% $SiO_2$ | 58.0 |
| 9  | 80%-$Mg_{4.5}Ni_{2.5}Fe_3Bi_1P_{0.5}Mo_{12}O_{51}$-20% $SiO_2$ | 67.7 |
| 10 | " (b) | 72.9 |
| 11 | 80%-$Mg_{4.5}Ni_{2.5}Fe_3Bi_1As_{0.5}Mo_{12}O_{51}$-20% $SiO_2$ | 71.5 |
| 12 | " (b) | 78.3 |
| 13 | 80%-$Mg_{4.5}Co_{2.5}Fe_3Bi_1P_{0.5}Mo_{12}O_{51}$-20% $SiO_2$ | 64.0 |
| 14 | 80%-$Mg_2Ni_{2.5}Co_{4.5}Fe_1Bi_1P_{0.5}Mo_{12}O_{53}$-20% $SiO_2$ | 63.6 |
| 15 | 80%-$Mg_{0.1}Ni_{10}Co_{0.3}Fe_1Bi_1P_1Mo_{12}O_{57}$-20% $SiO_2$ | 60.2 |
| 16 | 80%-$Ca_2Ni_{2.5}Co_{2.5}Fe_3Bi_1P_{0.5}Mo_{12}O_{53}$-20% $SiO_2$ (b) | 70.4 |
| 17 | 80%-$Zn_{4.5}Ni_{2.5}Fe_3Bi_1P_{0.5}Mo_{12}O_{51}$-20% $SiO_2$ (b) | 64.9 |
| 18 | 80%-$Cd_{4.5}Ni_{2.5}Fe_3Bi_1P_{0.5}Mo_{12}O_{51}$-20% $SiO_2$ (b) | 58.9 |
| 19 | 60%-$Mg_{4.5}Ni_{2.5}Fe_3Bi_1P_{0.5}Mo_{12}O_{51}$-40% $SiO_2$ (b) (c) (Extruded) | 73.1 |

(a) 4 moles of $H_2O$ per mole of propylene were added to the feed
(b) contact time was 6 seconds
(c) attrition-resistant catalyst —2-stage addition of $SiO_2$ support

TABLE II

CONVERSION OF ISOBUTYLENE TO METHACRYLONITRILE
Fixed-Bed Reactor
Reaction Temperature: 715° F.  Contact Time: 2.9 seconds
Feed Ratio (Molar): $IC_4^=/NH_3/Air = 1/1.5/11$

| Example | Catalyst Composition | (Mole Basis) % Per Pass Conversion to Methacrylonitrile |
|---|---|---|
| 20 | 50%-$Fe_{4.5}Bi_{4.5}PMo_{12}O_{52}$-50% $SiO_2$ | 34.1 |
| 21 | 80%-$K_{0.07}Mg_{4.5}Fe_4Bi_2P_{0.5}Mo_{12}O_{51}$-20% $SiO_2$ | 57.7 |
| 22 | 80%-$Mg_{4.5}Ni_{2.5}Fe_3Bi_1P_{0.5}Mo_{12}O_{51}$-20% $SiO_2$ | 50.9 |

We claim:

1. A catalyst composition consisting essentially of a complex of the catalytic oxides of iron, bismuth, molybdenum, and at least one metal selected from Group IIB of the Periodic Classification as essential components, optionally the oxides of cobalt, nickel, phosphorus, arsenic and an alkali metal, and having the following formula:

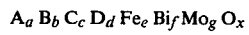

$$A_a B_b C_c D_d Fe_e Bi_f Mo_g O_x$$

wherein
A is an alkali metal;
B is one or more of the elements selected from the group consisting of nickel and cobalt;
C is phosphorus or arsenic or both; and
D is at least one element selected from Group II B of the Periodic Classification of Elements; and
wherein
a is a number from 0 to less than 0.1;
b is a number from 0 to 12;
c is a number from 0 to 3;
d is a number from 0.1 to 10;
e and f are each a number from 0.1 to 6;
g is a number from 8 to 16; and
x is a number determined by the valence requirements of the other elements present.

2. The composition of claim 1 wherein B in the catalyst formula is cobalt and nickel and b is a positive number.

3. The composition of claim 1 wherein B in the catalyst formula is nickel and b is a positive number.

4. The composition of claim 1 wherein B in the catalyst formula is cobalt and b is a positive number.

5. The composition of claim 1 wherein said catalyst consists of:

$$A_a B_b C_c D_d Fe_e Bi_f Mo_g O_x.$$

6. The catalyst of claim 1 prepared by the process comprising the steps of:
(a) activating a mixture of said catalyst and from 0 to 60 percent by weight of the total of a support material at a temperature of from about 1000° F. to about 2000° F. in an oxidizing atmosphere, and reducing the resulting catalyst to a fine powder and
(b) mixing the powder from (a) with an aqueous slurry of the remaining support material, drying and heat-treating the resulting mixture at a temperature of from about 750° F. to about 2000° F.